United States Patent [19]
Trott

[11] Patent Number: 5,472,452
[45] Date of Patent: Dec. 5, 1995

[54] RECTILINEAR ANCHOR FOR SOFT TISSUE FIXATION

[75] Inventor: Arthur F. Trott, Largo, Fla.

[73] Assignee: Linvatec Corporation, Largo, Fla.

[21] Appl. No.: 297,741

[22] Filed: Aug. 30, 1994

[51] Int. Cl.$^6$ ................................. A61B 17/04
[52] U.S. Cl. ................... 606/232; 606/72; 606/74; 24/297
[58] Field of Search ............... 606/72, 74, 232; 24/297, 324, 662

[56] References Cited

U.S. PATENT DOCUMENTS

| | | | |
|---|---|---|---|
| 4,312,614 | 1/1982 | Palmer et al. | 24/297 |
| 4,632,100 | 12/1986 | Somers et al. | 606/232 |
| 4,709,949 | 1/1987 | Umezawa et al. | 24/662 |
| 4,726,722 | 2/1988 | Wollar | 24/297 |
| 4,741,330 | 5/1988 | Hayhurst | 606/232 |
| 4,778,320 | 10/1988 | Nakama | 24/662 |
| 4,883,382 | 11/1989 | Mushya | 24/297 |
| 4,890,966 | 1/1990 | Umezawa | 24/297 |
| 4,899,743 | 2/1990 | Nicholson et al. | 606/232 |
| 4,968,315 | 11/1990 | Gatturna | 606/232 |
| 5,037,422 | 8/1991 | Hayhurst et al. | 606/232 |
| 5,100,417 | 3/1992 | Cerier et al. | 606/232 |
| 5,102,421 | 4/1992 | Anspach, Jr. | 606/232 |
| 5,141,520 | 8/1992 | Goble et al. | 606/232 |
| 5,156,616 | 10/1992 | Meadows et al. | 606/232 |
| 5,176,682 | 1/1993 | Chow | 606/232 |
| 5,224,946 | 7/1993 | Hayhurst et al. | 606/232 |
| 5,376,101 | 12/1994 | Green et al. | 606/232 |

*Primary Examiner*—Gary Jackson

[57] ABSTRACT

A method and bone anchor assembly apparatus for attaching suture material to bone tissue includes a hollow anchor body having a rectilinearly-bounded transverse cross-section with a maximum dimension corresponding to the diameter of the bone tunnel drilled to receive the anchor. A longitudinally displaceable plug received within the anchor body is contoured to interact with inwardly biased bone tissue engaging barbs formed on the sides of the anchor body, defining a first position wherein the barbs are allowed to uninterferingly retract within the anchor body and a second position wherein the plug forces the barbs outward into engaging contact with the bone tunnel sidewalls. Suture material is passed around the anchor assembly, through a transverse slot defined in the assembly distal end and the plug is positioned in the first position with barbs retracted. The assembly is inserted into the bone tunnel and the plug is urged into the second position with barbs engaged in bone tissue. Removal of the assembly is made possible by urging the plug back into the first position.

19 Claims, 3 Drawing Sheets

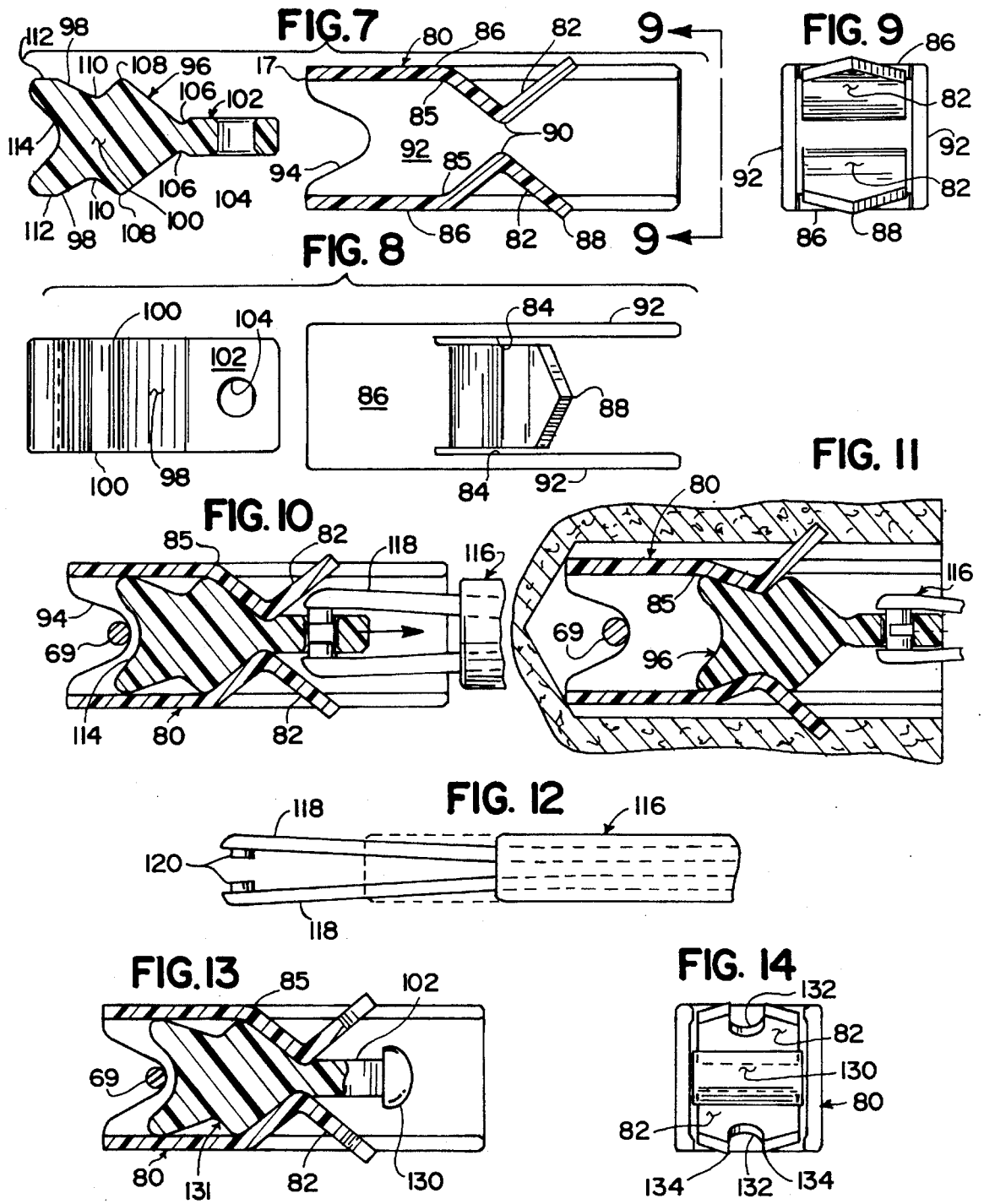

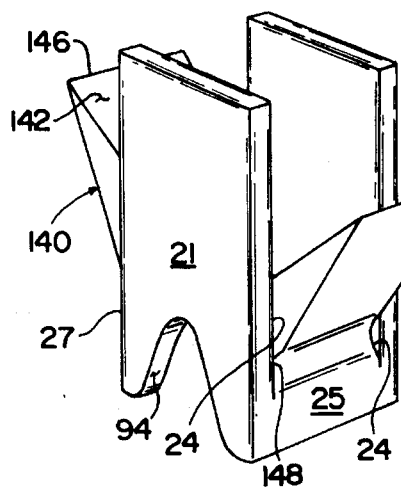
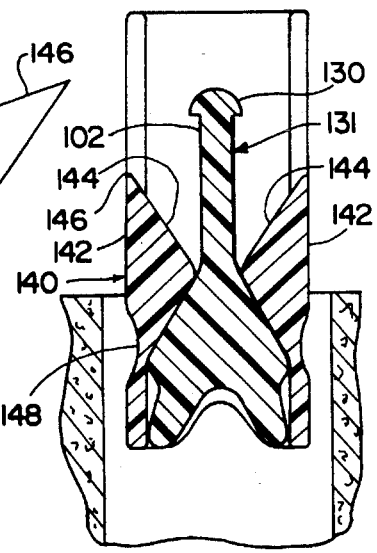
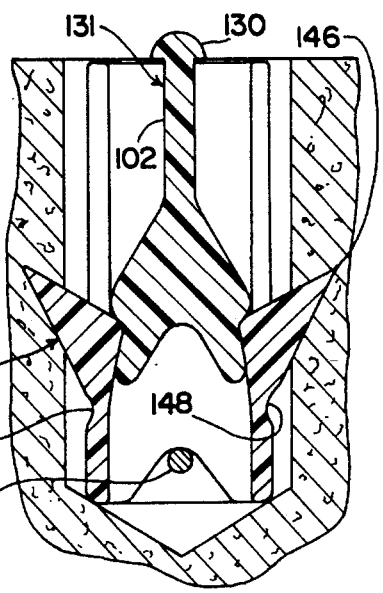
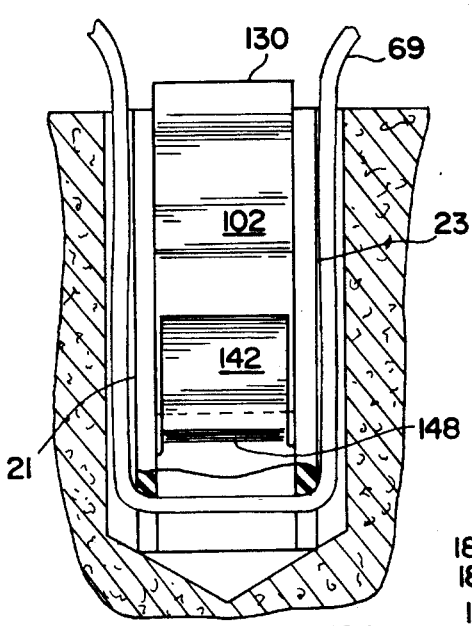
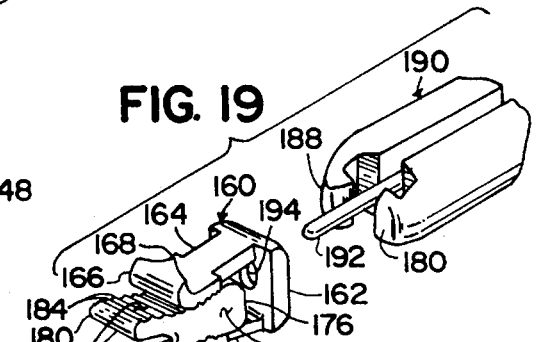
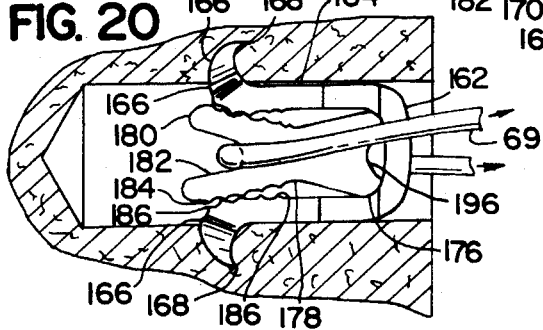
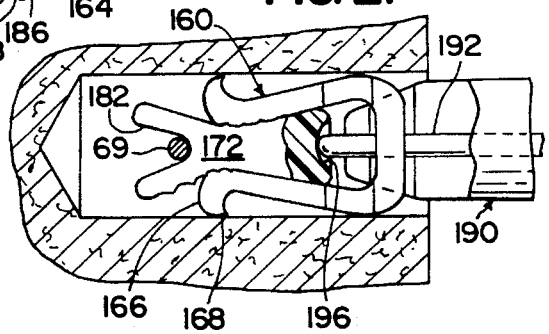

RECTILINEAR ANCHOR FOR SOFT TISSUE FIXATION

BACKGROUND OF THE INVENTION

1. Technical Field

The present invention pertains to methods and apparatus utilized in surgical procedures involving fixation of soft tissue to bone and, more particularly, to a novel method and apparatus for anchoring sutures to bone tissue to permit the aforesaid fixation.

2. Discussion of the Prior Art

As part of various endoscopic or arthroscopic surgical procedures, it is necessary to permanently attach a suture to bone tissue. For example, in certain procedures requiring suturing of soft tissue (e.g., muscle, cartilage, tendons, ligaments, etc.) to bone tissue, the suture must be anchored to the bone tissue before suturing can proceed. The prior art includes numerous suture anchors adapted to be secured in pre-drilled holes or tunnels in the bone tissue, and most of these anchors have one or more disadvantageous characteristics. Some prior art suture anchors are required to be hammered into a bone tunnel. These anchors are exemplified by U.S. Pat. Nos. 5,102,421 (Anspach, Jr.); No. 5,141,520 (Goble et al); and No. 5,100,417 (Cerier et al). Hammering (or impacting as it is often described) has the disadvantage of potential trauma and damage to surrounding bone tissue, and has limited applicability where the location of the bone tunnel is not axially aligned with an arthroscopic portal to direct transmission of the impacting force through an impactor to an anchor.

Some prior art suture anchors are threadedly mounted in the bone tunnel, as exemplified by U.S. Pat. Nos. 5,156,616 (Meadows et al) and No. 4,632,100 (Somers et al). The screw insertion procedure tends to be time-consuming in that a pilot hole must first be drilled into the bone and then the hole may have to be tapped to receive the screw. If, as sometimes happens, the surgeon determines that the tunnel is not ideally located, the drilling and tapping of another pilot hole becomes necessary, thereby requiring additional steps in an already lengthy procedure.

Many suture anchors involve an insertion procedure wherein a relatively large insertion tool must partially enter the bone tunnel along with the anchor, thereby requiring a larger diameter tunnel than would be necessary for the anchor alone. Examples of such suture anchors are found in U.S. Pat. Nos. 5,037,422 (Hayhurst et al); No. 4,741,330 (Hayhurst); No. 4,968,315 (Gatturna) and No. 4,899,743 (Nicholson et al). Large diameter bone tunnels for receiving suture are undesirable in many applications, particularly where the bone itself is relatively small. In addition to the insertion tool size, some anchors themselves must be so large as to limit the degree to which bone tunnel diameters can be decreased. An example of such an anchor is found in U.S. Pat. No. 5,224,946 (Hayhurst et al).

Most of the foregoing exemplar prior art suture anchors suffer from the disadvantage of being automatically deployed upon initial insertion into the bone tunnel. Specifically, such anchors typically have permanently projecting resilient barbs, or the like, that are forced into the tunnel during initial insertion and preclude proximally directed movement within the tunnel after at least one barb engages the surrounding bone tissue during insertion. If the particular bone tunnel turns out to be unsuitable, either because of location or configuration, the surgeon may not recognize this until after the anchor has been inserted. With many prior art anchors there is no possibility of removing the inserted anchor; thus, a new tunnel must be drilled and a second anchor inserted. Accordingly, two (or possibly more) anchors may be left at the surgical site, and only one of the anchors is functional. This problem is addressed in U.S. Pat. No. 5,176,682 (Chow) wherein a generally cylindrical suture anchor is disclosed as having normally retracted fins capable of being selectively projected radially to engage the bone tunnel wall in a barb-like manner. Selective projection of the fins is effected by hammering a pin axially through the anchor to force the fins radially outward. Prior to hammering the pin, the inserted anchor is readily removable from the bone tunnel, thereby permitting the surgeon to test the adequacy of the drilled tunnel and its location. If a tunnel is unsatisfactory, the anchor can be removed, rather than being left in place. Although this technique solves the problem of having an unused anchor left in an unsatisfactory tunnel, it has some other disadvantages. In particular, the cylindrical body of the Chow anchor must be specially contoured with longitudinally extending recessed channels for accommodating the anchored suture or ligament without compressing it between the anchor and the bone tunnel wall. Such compression could unduly stress the suture or ligament and cause it to tear. Occasionally, the suture becomes dislodged from the recess and becomes stressed in spite of the presence of the recesses. Moreover, the channels add complexity to the manufacture of the anchor. In addition, the actuator pin for the Chow anchor is not positively retained by the anchor, leaving the possibility that the pin will inadvertently become dislodged, permitting the fins to retract and the anchor to become disengaged from the tunnel. Also, the insertion tool threadedly engages the anchor during insertion, thereby requiring multiple rotations of the inserted tool to disengage it from the anchor after insertion. Still further, the insertion procedure for the Chow anchor requires a mallet, in addition to the insertion tool, to hammer the pin through the insertion tool (serving as a guide) and into the anchor. Thereafter, the insertion tool must be removed in a manner described ambiguously at best in the Chow patent. The installation procedure and tools tend to be unnecessarily complicated.

OBJECTS AND SUMMARY OF THE INVENTION

It is therefore an object of the present invention to provide improved methods and apparatus for anchoring suture, and the like, to bone.

It is another object of the present invention to provide a suture anchor of the general type disclosed in the aforementioned Chow patent, but wherein the need for channels to accommodate suture is eliminated without subjecting the anchored suture to compression stress between the anchor and bone tunnel wall.

Another object of the invention is to provide a suture anchor of the type described wherein the anchor pin is positively retained in the anchor to prevent the anchor fins from retracting.

It is still another object of the invention to provide a suture anchor of the type described wherein the procedure and equipment required for insertion are significantly simplified.

Yet another object of the invention is to provide a suture anchor of the type described wherein the anchor, upon initial insertion into a bone tunnel, is positively gripped therein prior to expanding the fins, whereby the anchor can be removed forcefully by pulling it from the tunnel.

The aforesaid objects are achieved individually and in combination, and it is not intended that the invention be construed as requiring that two or more of said objects be combined.

In accordance with the present invention a suture anchor assembly is provided with a rectilinearly bounded transverse cross-section having its diagonal dimension corresponding substantially to the diameter of a bone tunnel. Elongated straight edges of the anchor thus contact the bone tunnel wall, and space between those edges is free to accommodate the anchored suture without compression. Resilient barbs on opposite side walls of the anchor body are bent to first converge and then diverge in a proximal direction to form inwardly facing knees. A plug is disposed within the hollow interior of the anchor body prior to installation and includes a contoured periphery configured to be retained in snap fit engagement in two different longitudinal positions within the anchor body. In a first position, corresponding to pre-installation of the anchor, the knees are relatively close to one another and the free ends of the barbs are transversely retracted. In a second position the knees are spread apart by the plug, thereby forcing the proximally directed free ends of the barbs outward to engage the bone tunnel wall and prevent removal of the anchor. The plug is configured at its proximal end to receive an insertion tool capable of holding the plug and anchor body during insertion into the bone tunnel, and of exerting longitudinal force on the plug to move it to the second described position wherein the barbs are deployed for anchor installation. Disengagement of the insertion tool from the plug is accomplished simply and quickly. In one embodiment the insertion tool tip is merely slidably received in a bore extending distally from the proximal end of the plug. In alternative embodiments the proximal end of the plug is configured to be engaged between jaws of the insertion tool, thereby permitting the plug to be pulled out of the anchor body, causing radial retraction of the barbs and permitting removal of the previously installed anchor from the bone tunnel.

The anchor may taper distally to permit the assembly to be inserted into the bone tunnel in a wedge-like manner whereby it squeezes against the bone to permit positive orientation of the anchor prior to permanent installation by means of distal movement of the plug.

The above and still further objects, features and advantages of the present invention will become apparent upon consideration of the following detailed description of specific embodiments thereof, particularly when considered in conjunction with the accompanying drawings wherein like reference numerals in the various figures are utilized to designate like components.

BRIEF DESCRIPTION OF THE DRAWINGS

FIG. 7 is an exploded view in longitudinal section of an anchor assembly constituting a second embodiment of the present invention.

FIG. 8 is an exploded side view in elevation of the assembly of FIG. 7.

FIG. 9 is an end view in elevation taken along lines 9—9 of FIG. 7.

FIG. 10 is a view in longitudinal section of the assembly of FIG. 7 shown engaged by the jaws of an insertion tool.

FIG. 11 is a view in longitudinal section of the assembly of FIG. 7, engaged by the insertion tool, with the assembly installed in a bone tunnel.

FIG. 12 is a side view in elevation of a portion of the insertion tool of FIGS. 10 and 11.

FIG. 13 is a view in longitudinal section of an anchor assembly constituting a third embodiment of the present invention.

FIG. 14 is an end view of the assembly of FIG. 13.

FIG. 15 is a view in perspective of an anchor body according to a fourth embodiment of the present invention.

FIG. 16 is a view in longitudinal section of an anchor assembly according to the fourth embodiment of the present invention shown during insertion into a bone tunnel.

FIG. 17 is a view in longitudinal section of the anchor assembly of FIG. 16 shown installed in a bone tunnel.

FIG. 18 is a side view in elevation of the installed assembly of FIG. 17.

FIG. 19 is an exploded view in perspective of still another embodiment of a suture anchor assembly of the present invention.

FIG. 20 is a view in longitudinal section of the assembly of FIG. 19 installed in a bone tunnel.

FIG. 21 is a view in longitudinal section of the assembly of FIG. 19 shown prior to installation in a bone tunnel.

DESCRIPTION OF THE PREFERRED EMBODIMENTS

Figure 1:
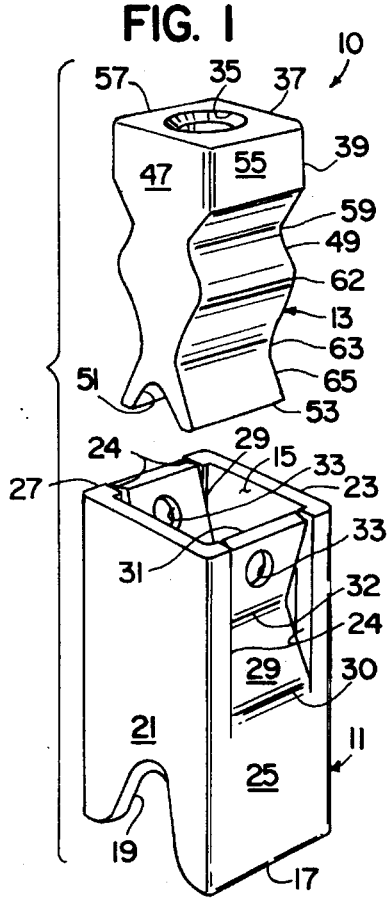
FIG. 1 is an exploded view in perspective of a first embodiment of a suture anchor assembly of the present invention.

Referring to FIGS. 1–6 of the accompanying drawings, a suture anchor assembly 10 of the present invention includes an anchor body 11 and an actuator plug 13. Anchor body 11 is a hollow four-sided member having an open proximal end 15 and an open distal end 17. The anchor body may be described as rectilinear rather than tubular in that the transverse perimeter is defined by straight intersecting lines rather than a continuous circle. In the illustrated embodiment the transverse periphery defines a square cross-section having equal width and length and a diagonal distance generally equal to the diameter of the borehole bone tunnel into which it will be inserted. It will be appreciated from the following description that three-sided, five-sided or any poly-sided cross-sections may be employed as well. Moreover, although a square periphery has advantages, the sides are not required to be of equal length. In this regard what is important is that the insertion of any straight-sided anchor assembly into a cylindrical predrilled hole having a diameter generally equal to the maximum cross-sectional dimension of the anchor provides clearance space defined between the straight outer sides of the anchor and the curved inner surface of the cylindrical bore-hole for freely and uncrimpingly accepting passage of suture material.

Arcuate slots 19 are defined transversely across the distal ends of a first pair of opposed flat anchor sidewalls 21 and 23 to provide relief space for suture passage.

Pairs of spaced longitudinal slots 24 extending distally from the proximal ends of the second pair of opposed sidewalls 25 and 27 define fins or barbs 29 extending along the proximal portion of anchor body 11. Barbs 29 resiliently extend proximally inward from a hinge 30 formed between the distal ends of slots 24 to about the midlength of the barb and then extend proximally outward terminating in tissue engaging leading edges or points 31. Note that for the purpose of this description as well as in these practical applications, the terms points and leading edges are used interchangeably. The angled mid-portions of the barbs define inwardly facing knees 32 extending into the open central portion of anchor body 11. Holes 33 are defined in the proximal portions of barbs 29 to receive an anchor removal tool as will be described hereafter.

Figure 2:
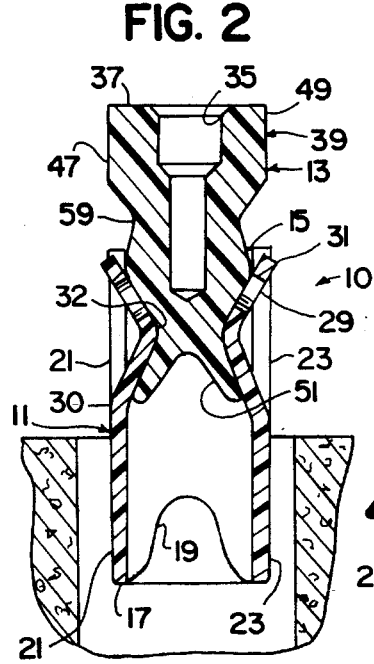
FIG. 2 is a view in longitudinal section of the assembly of FIG. 1 showing the assembly during its insertion into a bone tunnel.

Referring to FIG. 2, actuator plug 13 is a solid body having a counterbored hole 35 defined therein extending distally from the proximal end along the plug longitudinal axis for receiving the distal end of an insertion tool. The proximal portion 39 of plug 13 is rectangular in cross-section having a major dimension equal to the outer dimension of square cross-section anchor body 11 and a minor dimension equal to or slightly smaller than the inner dimension of square hollow anchor body 11. The opposed minor axis sides 47 and 49 extend distally parallel to slotted sides 21 and 23 respectively of body 11 and an arcuate slot 51 extends transversely across the distal end 53 of plug 13 providing a retaining channel through which suture material is passed.

The opposed major axis sides 55 and 57 of plug 13 extend distally parallel to anchor sides 25 and 27 for a distance slightly less than the distance between barb knees 32 and anchor open proximal end 15, then are angled distally inward to a first proximal narrowed section 59 having separation width somewhat less than the width of the anchor body interior. Sides 55 and 57 then flair distally outward to a first proximal expanded section 62 having width approximately equal to the anchor body interior width, then angle distally inward once more to a second distal narrowed section 63 having width substantially less than the anchor body interior width and finally distally outward, terminating at the distal end in a second distal expanded section 65 having width slightly less than the anchor body interior.

Figure 3:
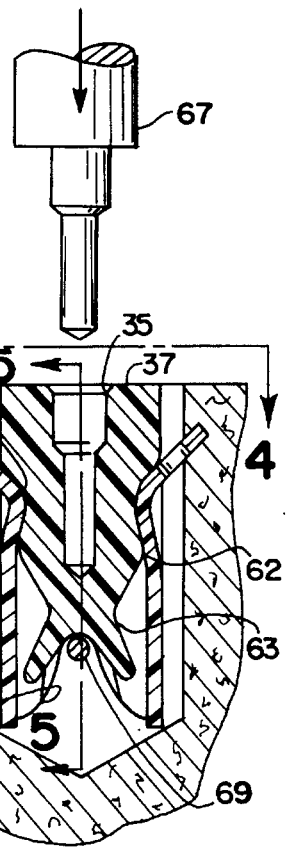
FIG. 3 is a view in longitudinal section of the assembly of FIG. 1 showing the assembly installed in a bone tunnel.
Figure 4:
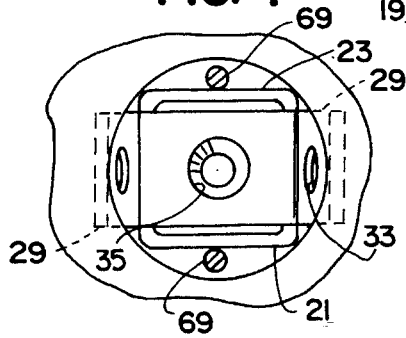
FIG. 4 is a top view in plan taken along lines 4—4 of FIG. 3.
Figure 6:
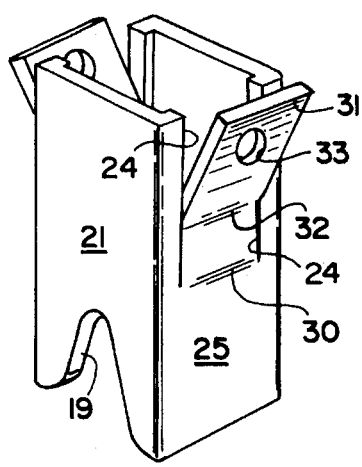
FIG. 6 is a view in perspective of the anchor body of the assembly of FIG. 1.
Figure 5:
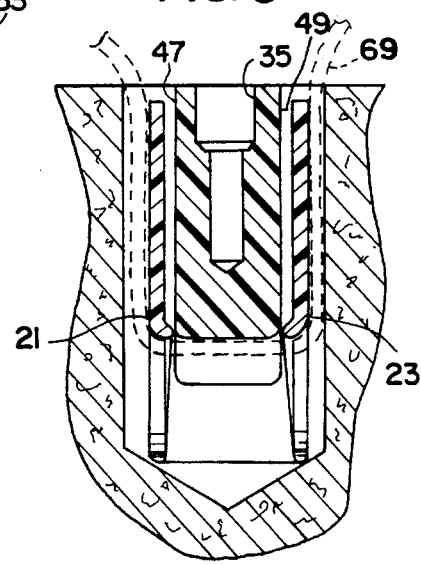
FIG. 5 is a view in section taken along lines 5—5 of FIG. 3.

In use actuator plug 13 is inserted into the open proximal end 15 of anchor body 11 with sides 47 and 49 of plug 13 aligned parallel to anchor sides 21 and 23, respectively. Distal expanded section 65 of plug 13 deflects knees 32 and resilient barbs 29 outward to permit distal passage of plug 13 until barb knees 32 engage distal narrowed section 63 in a snap fit at a first position and the barbs retract transversely into the assembly. An insertion tool 67, illustrated in FIG. 3, having a distal end configured to engagingly fit into counter-bored hole 35 in plug proximal end 37 is then used to deliver suture anchor assembly 10 to a bone site pre-bored to a depth approximately equal to the length of the assembly 10 and a diameter generally equal to the maximum transverse width of the assembly, in the case of a square anchor equal to the diagonal of the square assuring a friction fit between the hole and the anchor longitudinal edges. A length of suture material 69 is captured in arcuate slots 19 of anchor 11. The assembly is inserted into the hole until anchor distal end 17 is seated in the distal end of the borehole. Referring to FIGS. 3-5, the two ends of the suture material pass freely, that is, without compression, along the clearance space defined between flat sidewalls 21 and 23 and the borehole sidewall. Additional distal pressure exerted by the insertion tool then urges the plug distally forcing proximal expanded section 62 past barb knees 32, forcing barb points 31 outward into engaging penetrating contact with the bone of the borehole sidewall, as shown in FIG. 6. The plug seats at a second position in a snap fit with knees 32 engaged in proximal narrowed section 59 with the upper surface 37 of plug 13 flush with the open proximal end 15 of anchor body 11 and with the proximal surface of the bore. The snap fit of the knees into the proximal narrowed section of the plug provides positive retention of the plug in the assembly to preclude inadvertent dislodgement.

The anchor assembly is then held firmly in place by the combination of the friction fit of the edges against the borehole sides and the gripping engagement of points 31 into the bone. The suture material 69 passes freely down one side of the assembly, through slots 19 in anchor 11 and slot 51 in plug 13 passing under the anchor assembly and then back along the opposite side to provide a secure point of attachment for soft tissue with no compression of the suture material between the anchor and the bone.

In the event an anchor proves unsatisfactory, removal is effected by removing plug 13 by gripping the plug proximal end with compressible jaws and displacing proximally, then, using a separate anchor removal tool having opposed resilient end members configured to engage holes 33, the barbs are urged inward away from penetration into the adjacent bone material. The anchor body is then removed with a proximal displacement of the tool.

In a second embodiment, depicted in FIGS. 7–12, anchor body 80 is similar to first embodiment anchor body 11 except extended somewhat proximally. Barbs 82 formed by longitudinal slots 84 extend only partially in the proximal direction along a first pair of opposed anchor sides 86 and terminate in bone-engaging points 88, shown in FIG. 9. Barbs 82 resiliently extend proximally inward from a hinge 85 formed transversely across the distal ends of slots 84 to about midlength and extend proximally outward thereafter forming inwardly-facing knees 90. A second pair of opposed sides 92 has flat surfaces with arcuate slots 94 defined in the distal ends.

Actuator plug 96 has a first pair of opposed sides 98 contoured to engagingly interact with barb knees 90, as illustrated in FIGS. 7, 10 and 11, and a second pair of flat opposed sides 100 extending parallel to flat walls 92 of anchor body 80, shown in FIG. 8. An elongate flat proximal tongue section 102 of plug 96 has a thickness slightly larger than the undeflected knee separation distance. A circular passage 104 is defined in flat proximal section 102 extending between walls 98. Immediately distal of proximal section 102 plug sides 98 angle distally inward to form a short first narrowed proximal section 106 having a width approximately equal to the undeflected knee separation distance, then flair distally outward to a first expanded proximal section 108 having a width approximately equal to the inside width of anchor body 80. Plug sides 98 then angle distally inward to a second distal narrowed section 110 having a width slightly smaller than the inside width of anchor body 80, and finally flair once more distally outward to a second distal expanded section 112 once again having a width approximately equal to the anchor body inside width. An arcuate groove 114 is defined across the distal end of plug 96 extending between flat opposed sides 100.

In use plug 96 is inserted tongue section first into the open distal end 17 of anchor body 80, with the flat tongue section 102 extending proximally beyond the inward knees 90 of the barbs and with plug 96 held in a first position by the detent-like snap fit engagement of the inwardly urged knees with narrowed section 106. Suture material 69 is passed around the distal end of anchor body 80 and captured by slots 94. The assembly is grasped by an insertion tool 116 shown in FIGS. 10–12, having selectively compressible opposed gripping jaws 118 terminating in inwardly directed co-axially aligned short cylinders 120 sized to grippingly engage opposite sides of circular passage 104. The tongue is thus grasped and the assembly is inserted in frictional fit into a predrilled bone tunnel, FIG. 10. The tongue is then urged proximally by the tool, forcing proximal expanded section 108 over knees 90 and deploying barb points 88 into surrounding bone tissue to secure the anchor in place, FIG. 11. The inward pressure of knees 90 against distal narrowed section 110 acts as a detent to snap fit the plug in a second position and to prevent inadvertent removal of plug 96 from anchor body 80.

A third embodiment, shown in FIGS. 13 and 14, replaces the through-passage 104 with a knob-like expanded section 130 defined on the proximal end of proximal tongue section 102 of actuator plug 131. Referring to FIG. 13, knob 130 provides a strong and convenient point of gripping engagement between the plug and compressible jaws of an insertion tool, avoiding any potential structural compromise engendered by the presence of through-passage 104. Arcuate slots 132 defined along the proximal center lines of barbs 82, illustrated in FIG. 14, provide two bone-tissue engaging points 134 on each barb to enhance the bonding of the anchor assembly to the bone tunnel.

A fourth embodiment, illustrated in FIGS. 15–18, combines an actuator plug 131 of the third embodiment with an anchor body, shown in FIG. 15, having solid hinged wedges 140 rather than inwardly directed resilient knees 32 formed in barbs 82. Wedges 140 have tapered opposed faces. Outer faces 142 are defined between slots 24 in opposed anchor body sidewalls 25 and 27 and inner faces 144 taper distally inward from sharp proximal leading edges 146 to a separation width between opposed wedges generally equal to the thickness of flat tongue section 102 of plug 131, then taper distally outward, returning once again to the inner wall of the anchor body. A slight narrowing of the anchor sidewalls along the distal ends of wedges 140 defines flexible hinges 148 about which wedges 140 rotate as the inwardly directed thickened wedge sections are urged outward by the proximal movement of actuator plug 131, as shown in FIGS. 16, 17 and 18. The replacement of relatively thin walled resilient barbs 82 with solidly formed wedges 140 affords a substantially more rigid and stronger interaction between the actuator plug and the bone tissue engaging sharp leading edges, or points, 146 of the wedges.

In a fifth embodiment, shown in FIGS. 19–21, the anchor body 160 has an open-ended box or U-shape formed by a flat generally square proximal end piece 162 and an opposed pair of sidewalls 164 extending generally distally from end piece 162. Sidewalls 164 are resiliently biased inward in the distal direction and have outwardly directed barbs 166 defined in the distal portions. Barbs 166 have bone-tissue engaging sharp points 168 formed in the distal ends. Actuator plug 170 has a bow-tie profile with a first pair of opposed parallel flat sides 172 aligned orthogonal to sidewalls 164 and a second pair of contoured sides 174 extending from an enlarged proximal section 176 to a narrowed midsection 178 and then to an enlarged distal section 180 with the contoured sides extending generally longitudinally along the inner sides of sidewalls 164. A slot 182 extends across the distal end of plug 170 between flat sides 172 configured to entrap and guide suture material 69. The outward facing sides 174 of plug 170 have a series of spaced ribs 184 extending between flat sides 172 sized to engagingly interact with similar ribs 186 formed in the inward facing adjacent opposed sides of anchor body sidewalls 164.

The narrowed midsection 178 of plug 170 has a depth or thickness generally equal to the minimum separation required between resiliently inwardly biased sidewalls 164 corresponding to a separation distance between barb points 168 equal to less than the diameter of a bone tunnel into which the anchor assembly is to be inserted.

In use, sidewalls 164 of anchor body 160 are urged divergently outward and plug 170 is positioned therebetween with narrowed midsection 178 aligned with the inwardmost projecting portions of sidewalls 164. Sidewalls 164 are permitted to contract, or converge, resiliently against plug 170, drawing barb points 168 inward. The proximal end piece 162 of anchor body 160 is grasped by opposed jaws 188 of an inserter tool 190, illustrated in FIGS. 19 and 21. A length of suture material 69 is captured in slot 182 and the anchor assembly and the assembly is inserted into a predrilled bone tunnel. When anchor positioning is satisfactory, the suture material is tensioned, as shown in FIG. 20, that is, pulled tightly against slot 182, forcing plug 170 proximally, simultaneously urging increasingly thick portions of enlarged distal section 180 proximally and exerting outward force against barbs 166 digging points 168 in bone wall. The interacting ribs 184 and 186 on the plug and the anchor body, respectively, act as a ratchet to prevent reverse slippage of the relative motion of the two parts and allow relaxed control over suture tensioning.

When satisfactory bone engagement is achieved, as can be readily tested using the compressible jaws 188, the jaws can be expanded to release the anchor assembly and the tool 190 can be withdrawn. The anchor may have sidewalls tapering, or narrowing, distally from a proximal cross-section somewhat larger in maximum transverse dimension than the borehole diameter to provide a wedge-like gripping of the anchor assembly against the borehole sidewall during insertion.

Should circumstances require removal of the assembly, the tool is reinserted, the flat proximal end 162 of the anchor body is grasped by the jaws of the inserter tool and a longitudinally extendable rod 192 slidably housed in tool 190 is directed through a passageway 194 formed in end piece 162 and into abutting relationship with a receiving cavity 196 formed in the proximal end of plug 170. Additional distal displacement of rod 192 forces plug 170 distally relieving the outward force exerted by enlarged section 180 of plug 170 against barbs 166 until the inward bias on sidewalls 164 disengages barb points 168 from the bone tunnel wall and the assembly is removed by proximal withdrawing of the assembly in the grasp of compressed jaws 188 of tool 190.

From the foregoing description, it will be appreciated that the invention makes available a novel method and apparatus for anchoring suture material to bone characterized by free passage of the suture material around and under the anchor to avoid crimping or compression of the suture material and by a simple procedure for easily inserting and removing bone anchors from a selected anchor cite.

In accordance with the present invention, it is believed that other modifications, variations and changes will be suggested to those skilled in the art in view of the teachings set forth herein. It is therefore understood that all such variations, modifications and changes are believed to fall within the scope of the present invention as defined by the appended claims.

What is claimed is:

1. A bone anchor assembly for attaching suture material to bone tissue comprising:

a hollow anchor body having a rectilinearly bounded transverse cross-section with a maximum diagonal dimension corresponding substantially to the diameter of a predrilled bone tunnel, said anchor body having at least one resilient barb defined along at least one longitudinal side, said at least one barb extending proximally inward from a transverse distal hinge area to an angled knee located intermediate to said hinge and the proximal end of said anchor body, said at least one barb extending proximally outward from said knee toward said proximal end and terminating in at least one bone-tissue engaging point;

a plug configured to fit slidingly within said hollow anchor body having an outer surface contoured to selectively receive said at least one barb knee in an inwardly projecting position whereby said bone-tissue engaging point is retracted within the perimeter of said anchor body, said plug outer surface also contoured to selectively urge said at least one barb knee outward whereby bone-tissue is engaged by said at least one point; and means for positioning said assembly in a predrilled bone tunnel and selectively displacing said plug within said anchor body to urge said at least one barb point into bone tissue engagement with said bone tunnel.

2. The bone anchor assembly of claim 1 wherein said anchor body has a slot for engaging suture material defined transversely across said anchor body distal end.

3. The bone anchor assembly of claim 1 wherein said plug has a slot for engaging suture material defined transversely across said plug distal end.

4. The bone anchor assembly of claim 1 where said anchor body at least one barb is configured to engagingly interact with inwardly displaceable arms of an anchor removal tool.

5. The bone anchor assembly of claim 1 wherein said anchor body cross-section is rectangular in shape.

6. The bone anchor assembly of claim 1 wherein said plug has a tongue section extending proximally beyond said at least one barb knee and having a transverse passageway defined therein for engaging a longitudinally displaceable insertion tool.

7. The bone anchor assembly of claim 1 wherein said plug has a tongue section extending proximally beyond said at least one barb knee and having a knob defined on the proximal end for engaging a longitudinally displaceable insertion tool.

8. A bone anchor assembly for attaching suture material to bone tissue comprising:

a hollow anchor body having a rectilinearly bounded transverse cross-section with a maximum diagonal dimension corresponding substantially to the diameter of a predrilled bone tunnel, said anchor body having at least one inwardly extending solid wedge member formed along at least one longitudinal side, wherein said at least one wedge member is resiliently attached to said anchor body by a hinge along the transverse distal end of said wedge member, said at least one wedge member having a bone-tissue engaging sharp proximal edge;

a plug configured to fit slidingly within said hollow anchor body having an outer surface contoured to selectively receive said at least one inwardly extending wedge member in a first inwardly projecting position whereby said tissue-engaging sharp proximal edge is retracted within the perimeter of said anchor body, and in a second inwardly projecting position whereby bone tissue is engaged by said at least one sharp proximal edge; and means for positioning said assembly in a predrilled bone tunnel and selectively displacing said plug within said anchor body to urge said at least one sharp proximal edge into bone tissue engagement with said bone tunnel.

9. The bone anchor assembly of claim 8 wherein said anchor body has a slot for engaging suture material defined transversely across said anchor body distal end.

10. The bone anchor assembly of claim 8 wherein said plug has a slot for engaging suture material defined transversely across said plug distal end.

11. The bone anchor assembly of claim 8 wherein said anchor body cross-section is rectangular in shape.

12. A bone anchor assembly for attaching suture material to bone tissue comprising:

an anchor body having a rectilinearly bounded transverse cross-section with a maximum diagonal dimension corresponding substantially to the diameter of a predrilled bone tunnel, said anchor body having two longitudinal sides in a generally U-shaped configuration open on the distal end, having a longitudinal through passage defined in said distal end, said sides having outwardly directed bone tissue engaging sharp points formed in the distal ends and being resiliently biased inward to retract said points within the perimeter of said anchor body; and a plug configured to fit slidingly between said longitudinal sides having an outer surface contoured to selectively receive said inwardly biased distal ends in said retracted position, said plug outer surface also being contoured to selectively urge said distal ends outward to engage bone tissue, said plug outer surface and said anchor body sides inner surfaces having transverse ribs to provide ratcheting mutual interaction during relative motion of said surfaces, said plug having a slot for engaging suture material defined transversely across said plug distal end; and means for positioning said assembly in a predrilled bone tunnel and selectively displacing said plug within said anchor body to urge said distal end sharp points into bone tissue engagement with said bone tunnel.

13. A method for anchoring suture material to bone tissue comprising the steps of:

(a) drilling a cylindrical tunnel into the bone at the point of desired attachment;

(b) passing a length of suture material around the distal end of a bone anchor having a rectilinearly bounded transverse cross-section defined by straight longitudinal anchor assembly sides and corresponding in maximum transverse diagonal dimension to the diameter of said cylindrical tunnel, said suture material passing through a slot transversely defined across the distal end of said anchor and extending proximally along two of said straight anchor sides;

(c) inserting said anchor into said tunnel, said straight longitudinal anchor assembly sides providing clearance space for passage of said suture material between said anchor and the sidewall of said tunnel; and (d) urging inwardly biased at least one barb formed along said anchor sides outwardly, driving sharp points formed on the distal ends of said at least one barb into bone tissue engaging contact with said tunnel sidewall.

14. The method of claim 13 wherein said barbs are urged outward by the distal movement of a plug configured to fit slidingly within said anchor and having contoured sides formed to selectively allow said inwardly biased barbs to retract into said anchor and to selectively urge said barbs outward into said bone tunnel sidewall.

15. The method of claim 14 further comprising the steps of
   (e) removing an unsuitably installed bone anchor by urging said plug proximally out of said assembly allowing inwardly biased barbs to retract disengagingly into said anchor; and
   (f) proximally urging said anchor out of said tunnel.

16. The method of claim 13 wherein said barbs are urged outward by the proximal movement of a plug configured to fit slidingly within said anchor and having contoured sides formed to selectively allow said inwardly biased barbs to retract into said anchor and to selectively urge said barbs outward into said bone tunnel sidewall.

17. The method of claim 16 further comprising the step of
   (e) removing an unsuitably installed bone anchor by urging said plug distally to a position allowing said inwardly biased barbs to retract disengagingly into said anchor; and
   (f) proximally urging said anchor out of said tunnel.

18. A method for anchoring suture material to bone tissue comprising the steps of:
   (a) drilling a cylindrical tunnel into the bone at the point of desired contact;
   (b) passing a length of suture material around the distal end of a plug;
   (c) inserting a plug into a hollow bone anchor body having a rectilinearly bounded transverse cross-section corresponding in maximum dimension to the diameter of said cylindrical tunnel, said plug being configured to fit slidingly within said anchor and having sides contoured to selectively allow inwardly biased barbs formed on the sides of said anchor body to retract into said body in a first position and to urge said barbs outwardly into bone tissue engaging contact with said bone tunnel sidewall in a second position;
   (d) positioning said plug in said first position;
   (e) passing a length of suture material around the distal end of said plug through a slot formed transversely across the distal end of said plug;
   (f) inserting said anchor body and plug into said bone tunnel, said suture material passing freely along the clearance space created between said anchor body rectilinear cross-section and said bone tunnel; and
   (g) proximally urging said plug into said second position to set said barbs into said bone tunnel sidewall by proximally tensioning said suture material.

19. The method of claim 18 further comprising the steps of
   (h) removing an unsuitably installed bone anchor by urging said plug distally into said first position to allow said barbs to disengagingly retract; and
   (i) proximally urging said anchor body and plug out of said tunnel.

* * * * *